United States Patent [19]

Altschuler et al.

[11] 4,070,683

[45] Jan. 24, 1978

[54] OPTICAL SURFACE TOPOGRAPHY MAPPING SYSTEM

[76] Inventors: Bruce R. Altschuler, 123 Thornell, San Antonio, Tex. 78235; John Taboada, 159 Ebbtide, San Antonio, Tex. 78227

[21] Appl. No.: 663,640

[22] Filed: Mar. 4, 1976

[51] Int. Cl.$^2$ .............................................. G03B 17/54
[52] U.S. Cl. ............................................ 354/77; 356/2
[58] Field of Search ....................... 354/77, 78; 355/2; 356/2, 112; 350/163, 3.5

[56] References Cited

U.S. PATENT DOCUMENTS

| | | | |
|---|---|---|---|
| 3,169,459 | 2/1965 | Friedberg et al. | 354/77 X |
| 3,594,583 | 7/1971 | Sheldon | 350/163 X |
| 3,695,749 | 10/1972 | Stapleton | 350/163 |
| 3,749,493 | 7/1973 | Macovski | 356/2 |

OTHER PUBLICATIONS

Time-Life, *Frontiers of Photography*, "Holograms in Color", 1972.
IBM Technical Disclosure, "Forming a Stereo View", Pennington et al., vol. 12, No. 3, 8-1969.

*Primary Examiner*—Edna M. O'Connor
*Attorney, Agent, or Firm*—Joseph E. Rusz; Julian L. Siegel

[57] ABSTRACT

A first laser beam is reflected from the front and rear surfaces of a partially silvered glass slab generating a diverging set of interference fringes which are collimated by a positive lens. A second set of fringes is generated by a second laser beam and second partially silvered glass slab and is positioned to project through the first slab and is collimated by the same positive lens. The second pattern is aligned coaxially and mutually perpendicular to the first pattern creating a rectangular parallopiped grid pattern projected upon an observed object.

5 Claims, 4 Drawing Figures

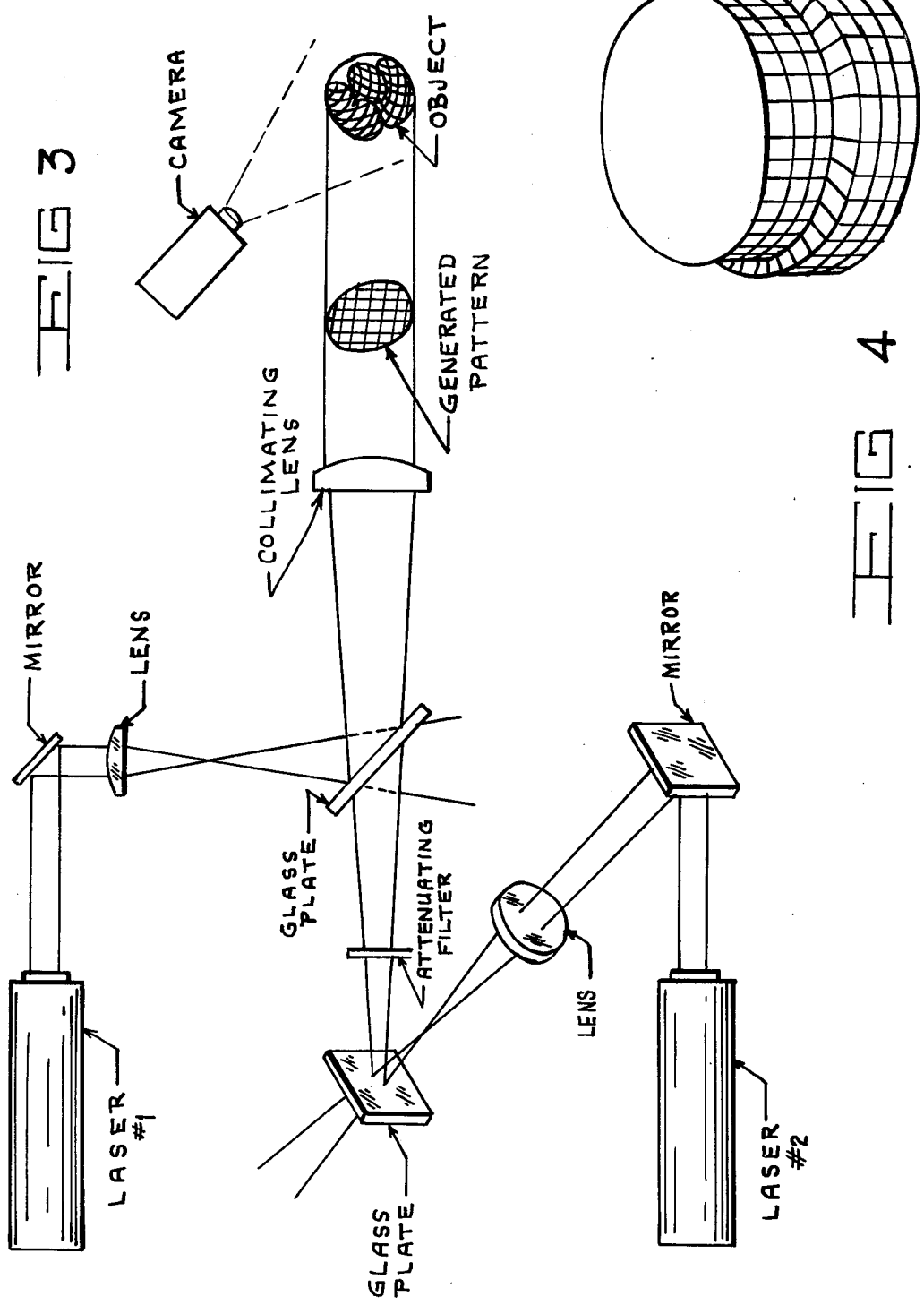

OPTICAL SURFACE TOPOGRAPHY MAPPING SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates to topographical mapping, and more particularly to a laser system for generating a grid pattern upon an observed object.

The invention provides a controllable high resolution rectangular fringe light pattern which can be made nondivergent as it propagates in space, and which can be projected on a surface for dimensional analysis and topography. The system provides a fast, efficient means for measuring, comparing and standardizing objects such as radar dishes, aircraft windscreens, fuselages, wing structures, aircraft parts, and tires. It may be applied to aerial terrain mapping, terrain following applications, and pattern recognition. Diagnostic surface mapping of living organisms and parts thereof, in-vivo and in-vitro, such as oral structures, ocular and facial structures, limbs, implants, mammaries, et cetera, is possible. Precision microscopic topography may be accomplished. Dynamic measurements of deformations or movements during applied stresses may be measured. Growth may be incrementally measured. In the particular applications of dentistry, the system provides a safe, practical, portable, clinical device for contouring oral structures in-vivo and intraorally, to produce a permanent contour record. This invention may provide more accurate contour data than do standard methods of taking impressions presently used in dentistry. The invention can also provide topographic image data for computer record storage and analysis, forensic and criminal identification, research, and for programming numerically controlled machines for fabrication of dental and medical prostheses, and health and industrial dies or forms.

Each set of parallel interference lines is generated optically as an optimum collimated fringe pattern of high contrast, through the use of a partially silvered glass plate, and a diverging coherent light beam. No physical grids or moving parts are required. The grid in this invention is merely a generated light/dark pattern.

The generation of rectangular or square parallelopiped optical fringe patterns for projection onto a surface to be analyzed topographically has not been achieved in the past. The sets of parallel lines may be adjusted optically to intersect at any angle from 0° to 90°, and the intensities, contrasts, or spatial frequencies of either or both sets may be adjusted for a particular specimen. Further, the grid pattern may be made diverging or nondiverging in space and the area of the grid pattern may be varied optically. The grid pattern, reflected off the specimen, may be recorded with photographic, holographic, cinematic, or electronic video equipment.

The system of the present invention may be used in-vivo and can be successfully used intra-orally for teeth and other oral structures. There are no safety hazards as all electrical equipment can be isolated from the subject. Laser power levels may be adjusted for complete safety for all areas of the body.

SUMMARY OF THE INVENTION

This invention records the surface topography of any given object. It may be used with complete safety for clinical in-vivo topographic mapping of living structures, including intraoral regions. The system optically generates a rectangular grid fringe pattern which remains nearly constant as it propagates through space. When this pattern is projected on a given surface the surface topography modifies the normal grid pattern. The system records the altered pattern by photography, video imaging, et cetera, for subsequent topographic analysis. The grid pattern and/or its spatial frequency may be adjusted for optimum recording of any size, texture, or surface configuration of a given object. The recorded data may be subsequently analyzed using appropriate data processing techniques.

In operation, a highly divergent beam from a monochromatic coherent source (such as a laser), is reflected from the front and back surfaces of a partially silvered glass slab. The partial reflections generate a diverging set of interference fringes with an angular periodicity dependent on the wavelength and divergence of the incident light and the slab thickness. The periodic array of light and dark fringes is collimated by a positive lens to form a parallel set of lines with a determinably high spatial frequency. A second set of fringes is generated by a separate diverging beam and partially silvered slab, but is projected through the first glass slab and collimated by a common positive lens. The second pattern is aligned coaxial and mutually perpendicular to the first pattern, thereby creating the final rectangular parallelopiped grid pattern in space. This parallelopiped grid pattern is projected on any given object and is systematically distorted by the varied topography of the object. A record of the pattern distortion can be obtained by photographic, holographic, cinematic or electronic video means. This record of the distorted pattern, taken from a well-determined angle, contains complete spatial information necessary to reconstruct the object to a precision limited only by the resolution of the fringe spacing of the pattern. The fringe spacing is adjustable, to allow use for different topographic applications or objects.

It is therefore an object of this invention to provide a system for generating interference patterns to form a grid pattern which can be projected in focus over a considerable distance.

It is another object to provide a controllable high resolution rectangular fringe light pattern which can be nondivergent as it propagates in space.

It is still another object to provide a system for measuring, comparing, and standardizing objects of varied shapes.

It is yet another object to provide a system for diagnostic surface mapping of living organisms.

These and other objects, features and advantages of the invention will become more apparent from the following description taken in conjunction with the illustrative embodiment in the accompanying drawings.

DESCRIPTION OF THE DRAWINGS

FIG. 3 is a schematic diagram showing an embodiment of the invention; and

FIG. 4 is a perspective view showing the gauging of a cylinder using the system of the invention.

DETAILED DESCRIPTION OF THE PREFERRED EMBODIMENT

Figure 1:
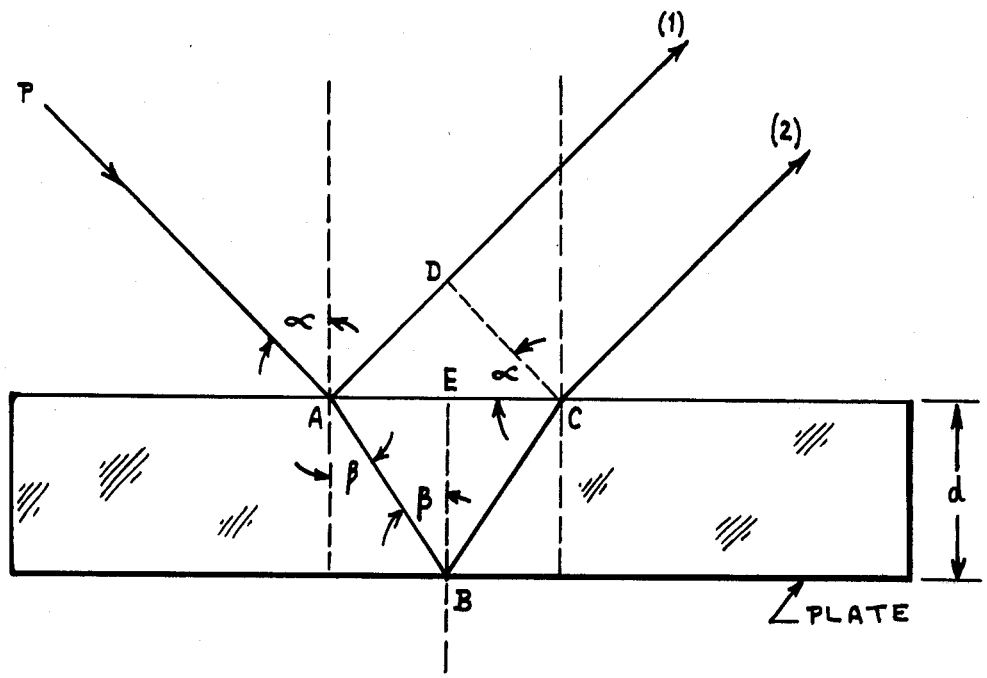
FIG. 1 is a diagram illustrating the principles of interference.

The generation of a rectangular fringe pattern for topographical applications is obtained through the interference of front and back reflections from a coated thin glass plate as shown in FIG. 1. A monochromatic beam from a point $p$ is incident at A on the plate and is partially reflected to D beam (1). The refracted beam (2) is reflected at B and emerges parallel to beam (1) at C. Depending on the difference in optical paths, beams (1) and (2) will create an interference fringe at infinity, as described by M. Born and E. Wolf in *Principles of Optics*, Pergamon Press, New York, 1965. The front and back reflected intensities are compensated with a partial silvering of the surface at B. The condition for optimum interference fringe formation is derived from this relationship and a system for rectangular grid generation is presented in this invention.

The condition for the creation of interference fringes is typically derived as follows: Referring to FIG. 1, define the path difference between the beams as $\delta_{12}$. Then:

$$\delta_{12} = n(AB + BC) - AD \tag{1}$$

where $n$ is the index of refraction of the plate and the index of the exterior medium is assumed to be one. Now:

$$AD = AC \sin \alpha = 2d \tan \beta \sin \alpha \tag{2}$$

and:

$$AB = BC = d/\cos \beta \tag{3}$$

From Snell's Law:

$$\sin \alpha = n \sin \beta \tag{4}$$

and from Equations (1), (2) and (3):

$$\delta_{12} = 2 n d/\cos \beta - 2d \tan \beta \sin = 2 n d \cos \beta \tag{5}$$

Due to a $\pi$ phase change at A, interference minima will occur at infinity whenever $$\delta_{12} = 2 n d \cos \beta = m\lambda, \tag{6}$$

where $n = 0, 1, 2$, etc. and $\lambda$ is the wavelength.
In terms of $\alpha$ using Equation (4):

$$\delta_{12} = 2 d (n^2 - \sin^2 \alpha)^{\frac{1}{2}} = m\lambda \tag{7}$$

Figure 2:
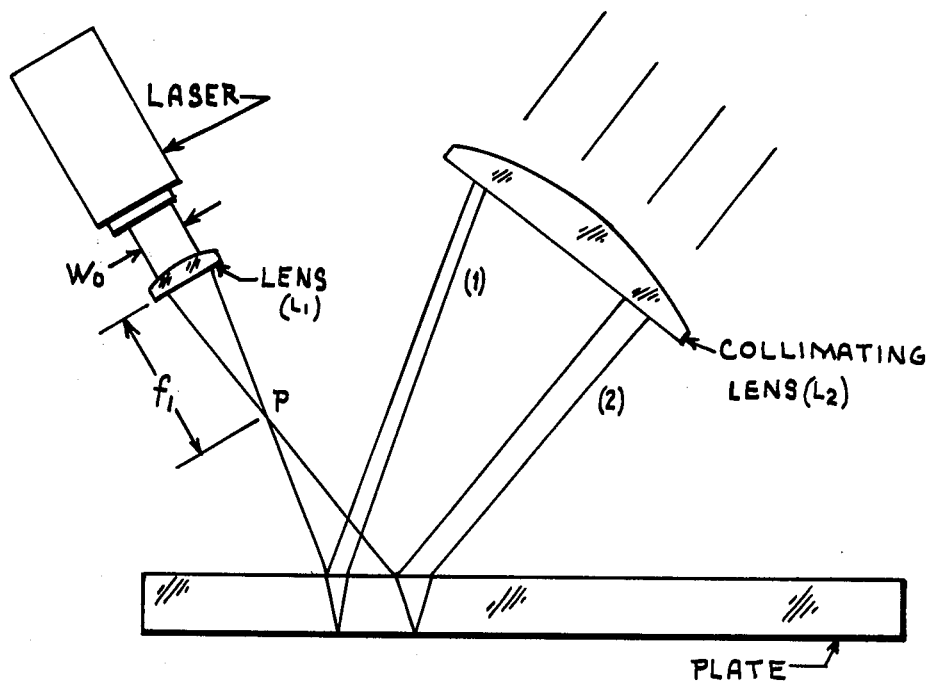
FIG. 2 is a diagram showing the generation of parallel fringes.

A set of fringes is generated as shown in FIG. 2 by a bundle of such rays from a point P at the focus of Lens ($L_1$) in the beam of a laser with beam diameter $W_o$. Here the angle $\alpha$ varies between the two extreme rays (1) and (2) of the diverging beam. The angular periodicity of the fringe minima can be calculated from the divergence of the beam at P by differentiating Equation 7:

$$\delta_{12} = d(n^2 - \sin^2 \delta)^{-\frac{1}{2}} \sin 2 \alpha \delta \alpha. \tag{8}$$

Fringe minima will occur with an angular period $\delta\delta$ resulting in a path change of $\lambda$, i.e.:

$$\delta \alpha = (\lambda/d) (n^2 - \sin^2 \alpha)^{\frac{1}{2}}/\sin 2\alpha \tag{9}$$

The total number of fringes (N) will depend on the total angular subtense of the beam from P, i.e.:

$$N = 2 \tan^{-1}(W_o/2f_1)/\delta\alpha$$

$$N = 2 d \tan^{-1}(W_o/2f_1)\sin 2q\alpha/\lambda\sqrt{n^2 - \sin 2\alpha} \tag{10}$$

where $\alpha$ is chosen as the average angle at the plate. Now if a second lens ($L_2$) is conveniently positioned as shown in FIG. 2, such that its focal length is equal to the optical path reflecting back through the plate to the point P, collimating of the fringe pattern will occur. The fringes leaving lens L2 will be parallel and undeviated with a spatial frequency given by the ratio of N to the beam diameter at Lens $L_2$.

Using the principle of fringe generation as described above, a diagram of an embodiment of the apparatus to generate a rectangular grid is shown in FIG. 3. Two lasers (1) and (2) are employed to generate separate fringe patterns, one projected through the glass plate of the other. The laser beam paths are arranged in particular planes for a rectangular grid pattern as shown.

The values and products presented in the following are by way of example and it is understood that other values may be used and remain within the scope of the invention.

The glass plates are standard 1 mm thick Inconel 0.2 O.D. filters positioned with the metal surfaces away from the diverging beam and at an angle of about 60° to the main optical axis running through the collimating lens. The diverging lenses have focal lengths of 48 mm. Lasers (1) and (2) are Spectra-Physics Helium-Neon lasers of lengths of 3 mW or less output. Both use standard 110-Volt electrical power. The collimating lens has a focal length of about 65 cm. An attenuating filter of the appropriate density may be introduced into the path of laser (2) to compensate its greater intensity. In an actual apparatus in operational configuration additional mirrors serve to bring the laser beams through their respective planes. The complete rectangular pattern is projected on a surface and is recorded by photography, holography, cinematography, or video imaging, at a convenient angle. Other lasers emitting other wavelengths or power outputs may be used, and suitable similar optics and lenses may be used, modified by wavelength or power requirements of the output lasers, and by the size of the object to be recorded.

The pattern attains its highest resolution when projected on a diffuse reflecting surface, for example, on the end of a piece of chalk. Machined metal surfaces without any preparation may nevertheless be gauged as in the case of a cylinder in FIG. 4. Molars or anterior teeth and gingiva can be coated with a harmless, nontoxic washable matt reflector of food coloring and adhesive. The coating very accurately assumes the contour of the teeth or soft tissue, and when the grid pattern is projected, clearly reveals the local topography. When the coating is not used the pattern may be seen, but with less clarity. The coating consists of a solution of water, propylene glycol, and FD and C Yellow No. 5, with a suspension of finely granulated tin oxide in the solution. A thick paste is made. Water and/or ethyl alcohol U.S.P. is added to thin the solution to a proper consistency which depends on the use required. Peppermint oil U.S. patent may be added in very small quantities for flavoring. Other suitable coatings, depending on the object studied, may be used. In the case of regular solids aligned along symmetrical angles with the grid pattern, the measurement is straight-forward as in the example of the cylindrical surfaces in FIG. 4. The radius of the top cylinder covers 16 fringe minima or 9.4 mm, which compares to that measured directly with a ruler. The height of the same cylinder extends 10 fringe minima or 5.9 mm which compares to the measured value using a ruler. More complex surfaces can be adequately analyzed by projecting on the photography or image record an orthogonal coordinate frame as is normally done for computer generated 3-D plots; the appropriate coordinates of a given point on the object is then given by the number of the two fringe minima and the projection onto an orthogonal Z-axis.

The correctness of Equation (10) for describing the fringe density is demonstrated by using the values for the various parameter characteristic of the prototype apparatus. Typical values for the parameters are:

$$d = 1.0 \times 10^{-3} m, n = 1.5, \alpha = 60°, \lambda = 0.63 \times 10^{-6} m, W_o \simeq 1.5 \times 10^{-3} m, \text{ and } f_1 = 48 \times 10^{-3} m.$$

These parameters can readily be optimized to increase the resolutions of the pattern. The degree of cross coherence between the two sets of fringes could be examined for its effect on the shape of of the intersection points. The example shown here is one with near zero cross coherence. It the cross coherence is increased, possibly the dark regions can be enhanced.

What is claimed is:

1. A system for projecting a rectangular grid pattern upon an object comprising:
   a. a first transparent slab, said first transparent slab having front and rear partially reflecting surfaces;
   b. a first source of coherent light directed at the first transparent slab generating a first beam of interference fringes;
   c. a second source of coherent light;
   d. a second transparent slab, said second transparent slab having partially reflecting front and rear surfaces and being positioned in the path of a second source of coherent light to generate a second beam of interference fringes directed into the first transparent slab at a right angle to that of the first source of coherent light to form a rectangular grid pattern upon the object; and
   e. means for recording the rectangular grid pattern upon the object.

2. A system for projecting a rectangular grid pattern according to claim 1 wherein the first and second coherent light sources are lasers.

3. A system for projecting a rectangular grid pattern according to claim 2 which further comprises a collimating lens interposed between the first transparent slab and the object.

4. A system for projecting a rectangular grid pattern according to claim 3 wherein the recording means is a photographic camera.

5. A system for projecting a rectangular grid pattern according to claim 4 wherein the first and second transparent slabs are glass having partial front and rear coatings of silver.

* * * * *